United States Patent
Chen et al.

(10) Patent No.: US 8,859,508 B2
(45) Date of Patent: Oct. 14, 2014

(54) APPLICATION OF 5-METHYL-1,3-BENZENEDIOL OR DERIVATIVES THEREOF IN THE PREPARATION OF MEDICINES AND FUNCTIONAL FOODS FOR TREATMENT OR PREVENTION OF DEPRESSION

(75) Inventors: Jijun Chen, Kunming (CN); Lin Xu, Kunming (CN); Jun Zhou, Kunming (CN); Jun Lu, Kunming (CN); Rongrong Mao, Kunming (CN); Meng Tian, Kunming (CN); Qixin Zhou, Kunming (CN); Xuemei Zhang, Kunming (CN); Yong Shen, Kunming (CN); Zhiyong Jiang, Kunming (CN); Aixue Zuo, Kunming (CN)

(73) Assignees: Kunming Institute of Botany, Chinese Academy of Sciences, Kunming (CN); Kunming Institute of Zoology, Chinese Academy of Sciences, Kunming (CN); Kunming Jingbiao Biosciences R&D Co., Ltd., Kunming (CN)

( * ) Notice: Subject to any disclaimer, the term of this patent is extended or adjusted under 35 U.S.C. 154(b) by 755 days.

(21) Appl. No.: 12/669,653

(22) PCT Filed: Jul. 25, 2008

(86) PCT No.: PCT/CN2008/071752
§ 371 (c)(1),
(2), (4) Date: Feb. 17, 2010

(87) PCT Pub. No.: WO2009/018747
PCT Pub. Date: Feb. 12, 2009

(65) Prior Publication Data
US 2010/0190730 A1   Jul. 29, 2010

(30) Foreign Application Priority Data
Aug. 3, 2007 (CN) .......................... 2007 1 0066088

(51) Int. Cl.
*A61K 31/70* (2006.01)
*A61K 31/05* (2006.01)
*A23L 1/30* (2006.01)
*A61K 31/7032* (2006.01)
*C07H 15/203* (2006.01)

(52) U.S. Cl.
CPC ................. *A23L 1/30* (2013.01); *A23L 1/3002* (2013.01); *A61K 31/05* (2013.01); *A61K 31/7032* (2013.01); *C07H 15/203* (2013.01)
USPC ............................................. 514/25; 514/731

(58) Field of Classification Search
None
See application file for complete search history.

(56) References Cited

U.S. PATENT DOCUMENTS 6,268,333 B1 * 7/2001 Okazaki et al. ................. 512/20

FOREIGN PATENT DOCUMENTS

| EP | 0474988 A1 | 3/1992 |
|----|-----------|--------|
| JP | 4-229152 A | 8/1992 |
| JP | 2004135522 A | 5/2004 |

OTHER PUBLICATIONS

Wu et al., Chem Pharm Bull, 53(8), 1065-67, 2005.*
Li Ning et al., "Study on the Chemical Constituents of *Curculigo orchioides*", Natural Product Research and Development, vol. 15 (2003), pp. 208-211.
Liu Qiang et al., "Analysis of Treemoss Concrete and Absolute Oil and its Application in Tobacco Flavoring", Tobacco Science and Technology/Tobacco Chemistry, No. 3 (2005), pp. 18-21.
ISR for PCT/CN2008/071752, (2008).
Fujikawa et al., "Studies on Antiseptics for Foodstuff. LXXIII. Studies on 3-Halogeno-4-hydroxy-benzoic Acid Esters, 4-Alkylresorcinol, 4-Arylresorcinol, 5-Alkyl-2,4-dihhydroxybenzaldehyde, 5-Alkyl-3-chloro-2,4-dihydroxybenzaldehyde,4-Aryl-6-chlororesorcinol and Phenylaminothioformic Acid Esters as a Preservative for Sake", Yakugaku Zasshi, vol. 92(6), pp. 768-771 (1972).
Sugiyama et al., "Hypocholesterolemic Action of Dietary Grifolin on Rats Fed with a High-choloesterol Diet", Biosci. Biotech. Biochem, vol. 58(1), pp. 211-212 (1994).
Zhao et al., "Study on the Chemical Constituents of *Curculigo orchioides*", Natural Product Research and Development, vol. 15(3), pp. 208-211 (2003).
Translation of EP474988A1 provided by Thomson Innovation, (1998).
Translation of JP2004135522A provided by Thomson Innovation, (2004).

* cited by examiner

*Primary Examiner* — Traviss C McIntosh, III
(74) *Attorney, Agent, or Firm* — Caesar, Rivise, Bernstein, Cohen & Pokotilow, Ltd.

(57) ABSTRACT

The present invention relates to the application of 5-methyl-1,3-benzenediol or its derivatives represented by Formula I; wherein the constituent variables are as defined herein or pharmaceutical compositions thereof containing them in the preparation of medicines or functional foods. The present studies indicate that 5-methyl-1,3-benzenediol or its derivatives represented by Formula I, wherein the constituent variables are as defined herein or pharmaceutical compositions thereof containing them show more significant antidepressant effects than fluoxetine or imipramine.

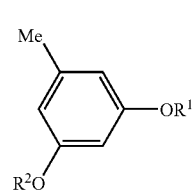

I

11 Claims, No Drawings

APPLICATION OF 5-METHYL-1,3-BENZENEDIOL OR DERIVATIVES THEREOF IN THE PREPARATION OF MEDICINES AND FUNCTIONAL FOODS FOR TREATMENT OR PREVENTION OF DEPRESSION

FIELD OF THE INVENTION

The present invention relates to the application of 5-methyl-1,3-benzenediol or derivatives thereof, or pharmaceutical compositions containing them in the preparation of medicines or functional foods.

BACKGROUND OF THE INVENTION

Depression is a common mental disorder that affects up to 20% of the total population. The following symptoms of depression are common: persistent or recurrent depressed mood, anxiety, agitation, sleep disorders, abnormal stress response, and cognitive functional impairment.

Over the past decades, many accepted animal models have been developed to evaluate the activity of antidepressants under the impetus of neuropharmacology. The most widely used models are the forced swim test and the tail suspension test in rodents. In recent years, many studies showed that constant darkness, sleep deprivation, and chronic unpredictable mild stress are etiological models for the occurrence of depression. These models laid the foundation for the study of antidepressants. Although the pathogenesis of depression is still not entirely clear, changes in hippocampal synaptic plasticity (for example, long-term potentiation) and its role in cognitive function may be one of the key mechanisms underlying depression.

5-Methyl-1,3-benzenediol (commonly known as orcinol) is usually used as an inhibitor of thermal polymerization in the processing of pyrolysis intermediates for organic synthesis. It is also a reagent for the specific determination of RNA. 5-Methyl-1,3-benzenediol and its derivatives have often been used as antioxidants and they possess a degree of antibacterial activity. So far, there is no report about their use in reducing depression, anxiety, agitation, sleep disorders, abnormal stress responses, or cognitive functional impairment.

SUMMARY OF THE INVENTION

The present invention relates to the application of 5-methyl-1,3-benzenediol or derivatives thereof, or pharmaceutical compositions containing them in the preparation of medicines or functional foods for treatment or prevention of depression. More specifically, the present invention is directed to 5-methyl-1,3-benzenediol or derivatives thereof for the treatment of depression or its related illnesses and the cause of these diseases.

The compounds of the present invention are 5-methyl-1,3-benzenediol or its derivatives thereof represented by Formula I:

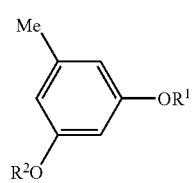

Wherein $R^1$ and/or $R^2$ are hydrogen, β-D-glucopyranosyl, β-D-glucopyranosyl-(1→6)-β-D-glucopyranosyl, mannosyl, 2,3,4,6-tetra-O-acetyl-β-D-glucopyranosyl, allosyl, galactosyl, rhamnopyranosyl, fucosyl, xylosyl, arabinosyl, acetyl, propionyl, benzoyl, cinnamoyl, succinyl, methyl, ethyl, propyl, butyl, or benzyl.

More preferably, the compounds of the present invention are 5-methyl-1,3-benzenediol or its derivatives represented by Formula II:

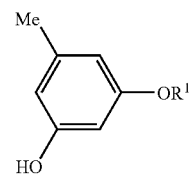

Wherein $R^1$ is hydrogen, β-D-glucopyranosyl, β-D-glucopyranosyl-(1→6)-β-D-glucopyranosyl, mannosyl, 2,3,4,6-tetra-O-acetyl-β-D-glucopyranosyl, allosyl, galactosyl, rhamnopyranosyl, fucosyl, xylosyl, arabinosyl, acetyl, propionyl, benzoyl, cinnamoyl, succinyl, methyl, ethyl, propyl, butyl, or benzyl.

More preferably, wherein $R^1$ is hydrogen; β-D-glucopyranosyl; β-D-glucopyranosyl-(1→6)-β-D-glucopyranosyl, which is listed as orcinol; or orcinol-1-O-β-D-glucopyranoside; or orcinol-1-O-[β-D-glucopyranosyl-(1-6)]-β-D-glucopyranoside.

More preferably, the compounds of the present invention are the derivatives of 5-methyl-1,3-benzenediol represented by Formula III:

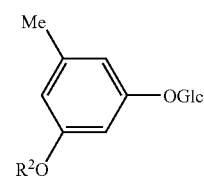

wherein $R^2$ is β-D-glucopyranosyl, β-D-glucopyranosyl-(1→6)-β-D-glucopyranosyl, 2,3,4,6-tetra-O-acetyl-β-D-glucopyranosyl, mannosyl, allosyl, galactosyl, rhamnopyranosyl, fucosyl, xylosyl, arabinosyl, acetyl, propionyl, benzoyl, cinnamoyl, succinyl, methyl, ethyl, propyl, butyl, or benzyl.

Especially, $R^2$ is β-D-glucopyranosyl, β-D-glucopyranosyl-(1→6)-β-D-glucopyranosyl, or rhamnopyranosyl.

More preferably, the compounds of the present invention are the derivatives of 5-methyl-1,3-benzenediol represented by Formula IV:

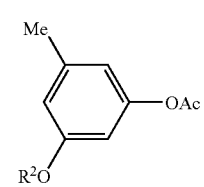

Wherein $R^2$ is β-D-glucopyranosyl, β-D-glucopyranosyl-(1→6)-β-D-glucopyranosyl, 2,3,4,6-tetra-O-acetyl-β-D-glucopyranosyl, mannosyl, allosyl, galactosyl, rhamnopyranosyl, fucosyl, xylosyl, arabinosyl, acetyl, propionyl, benzoyl, cinnamoyl, succinyl, methyl, ethyl, propyl, butyl, or benzyl.

Preferably, $R^2$ is 2,3,4,6-tetra-O-acetyl-β-D-glucopyranosyl, or acetyl.

Depression, as described in the Diagnostic and Statistical Manual of Mental Disorders, fourth edition (DSM-IV) published by the American Psychiatric Association, and the International Classification of Diseases, tenth edition (ICD-10), includes different subtypes of mental illnesses and disorders with: (1) depression and mood disorders, such as depression, mania, mixed mania, and hypomania; (2) depressive disorder, such as depressive disorder and bad mood; (3) other affective disorders, for example, caused by ill-health, which include different mental illnesses or subtypes of disorders with characteristics of depressive disorders and affective disorders caused by substances (for example, addictive drugs) or therapy (such as surgery, radiotherapy, or chemotherapy); (4) bipolar disorder or bipolar affective disorder, which contains two or more episodes of depression and hypomania, and alternating episodes of mania and depression.

Besides the symptoms of depression described in DSM-IV and ICD-10, the present invention also involves the treatment and prevention of circadian rhythm disorders, sleep disorders, chronic stress, anxiety, acute stress-induced impairment, or cognitive functional impairment or disorders.

Besides depression, the present invention also involves the therapy and prevention of diseases associated with circadian rhythm disorders, sleep disorders, chronic stress, anxiety, acute stress-induced impairment, or cognitive functional impairment or disorders. In addition, the present invention also involves the prevention and therapy of despair (for example, suicidal thoughts and behavior), mood disorders, and abnormal acute stress response.

Sleep and circadian rhythm disorders: Sleep disorder, a very common disease in patients with depression, is one of the contents of rating scales to evaluate the extent of depression. Circadian rhythm disorders refer to the most essential physiological function. The normal circadian rhythm is driven by alternating light and dark. Time difference, season, life habit, or inheritance can result in circadian rhythm disorders, which can further result in deficits of higher brain functions, such as depression and cognitive functional impairment. According to DSM-IV or ICD-10, sleep disorders are divided into three major categories: (1) dyssomnias, such as insomnia, hypersomnia, narcolepsy, breathing-related sleep disorders, and circadian-rhythm-related sleep disorders; (2) parasomnias, such as nightmare, sleep panic, and sleep walking; (3) health-related sleep disorders and sleep disorders caused by substances (for example, addictive drugs) or therapy (such as surgery, radiotherapy, or chemotherapy).

Anxiety is a very common symptom in patients with depression. It is one of guidelines to evaluate the extent of depression. Anxiety disorders include two major categories: (1) panic disorders, for example, agoraphobia, particular panic disorders (such as fear of particular animals, environments, or blood transfusion, social phobia, or obsessive-compulsive disorder), posttraumatic stress disorder, acute stress disorder, and extensive anxiety disorder; and (2) health-related anxiety disorders and substance-induced disorders (for example, addictive drugs) or therapy (such as surgery, radiotherapy or chemotherapy). Elevated plus maze and freezing behavior are widely used rodent models to evaluate the anti-anxiety activity of drugs.

Stress is defined in biological systems as any condition that seriously perturbs the physiological or psychological homeostasis of an organism. Stress is believed to be one of the main factors exacerbating or leading to many illnesses, such as mental disease and cognitive functional disorders. Stressful events may include a number of daily life events, and vary from person to person. Taking some substances, for example, addictive drugs or undergoing therapy, such as surgery, usually lead to abnormal stress responses. The commonly used biological indicators to evaluate stress include corticosteroid levels (such as corticosterone in rodents and cortisol in humans), which can lead to relevant acute stress-induced impairment, such as the damage of hippocampal synaptic plasticity as well as learning and memory. In animal experiments, commonly-used stress methods include foot shock and the elevated platform.

Cognition is one of the most important higher brain functions. It refers to learning, memory, language, thought, and mood. Depression is deemed to be a kind of cognitive disorder, and patients suffering from it have negative thoughts and mood automatically. In 1949, Hebb proposed the idea that synaptic modification is the basis of learning and memory. In 1973, this hypothesis was validated in experiments by Bliss et al. who discovered hippocampal long-term potentiation (LTP). However, so far no drug that regulates LTP directly has been used to treat depression in the clinic. Better and faster curative effects may be achieved by developing drugs that modify synaptic plasticity in treating depression, its related symptoms, and its causes.

5-Methyl-1,3-benzenediol or its derivatives can be directly used in the free form or in pharmaceutical compositions. The described pharmaceutical compositions contain 0.1-99% weight ratios of 5-methyl-1,3-benzenediol or its derivatives in pharmaceutically acceptable excipients.

As used herein, the term "pharmaceutical carriers and/or excipients" means one or more solid, semi-solid, or liquid diluent, filler, or formulation auxiliary of any type. The pharmaceutical compositions of 5-methyl-1,3-benzenediol or derivatives thereof are prepared to be various pharmaceutically acceptable excipients or dietarily acceptable supplements by well-known techniques in the field of pharmaceuticals and foods. The pharmaceutically acceptable excipients or dietarily acceptable supplements include sprays, aerosols, liquids such as injections, suspensions, emulsions, and syrups, and solids such as tablets, capsules and granules, or powder dissolved or suspended in liquid.

In the present invention, the methods of administration include injection or infusion (intravenous, intramuscular, intraperitoneal, or subcutaneous), and oral, sublingual, and mucosal administration.

The effective dosage of the active components (5-methyl-1,3-benzenediol or derivatives) to treat or prevent the above-mentioned diseases, their causes and symptoms is between 0.1 mg/adult/day and 12 g/adult/day, and the optimal dosage is 50-200 mg/adult/day.

The present invention reveals that 5-methyl-1,3-benzenediol or derivatives thereof, pharmaceutical compositions containing them in the preparation of medicines, and functional foods for the treatment or prevention of depression, provide a new choice for treating and preventing depression, and symptoms suggesting depression such as anxiety, stress, and cognitive impairment.

DETAILED DESCRIPTION OF THE INVENTION

The following examples describe the details of compounds and methods for the understanding and supplements of the invention, but these examples are not intended and should not be construed to limit in any way the invention set forth in the claims which follow thereafter. The compounds described in the present invention prepared by any other methods and their uses for treating depression, symptoms suggesting depression, and the etiological causes of depression are included in the present invention.

Wherein, orcinol (OR), orcinol-1-O-β-D-glucopyranoside (ORG) and orcinol-1-O-[β-D-glucopyranosyl-(1→6)]-β-D-glucopyranoside (ORGG) can be extracted from Curculigo orchioides Garr. Other derivatives of orcinol can be prepared by well-known techniques.

The specific process is as follows:

1. Orcinol can be reacted with the corresponding acetylated product of sugars wherein $R^1$ and/or $R^2$ are β-D-glucopyranosyl, β-D-glucopyranosyl-(1→6)-β-D-glucopyranosyl, mannosyl, allosyl, galactosyl, rhamnopyranosyl, fucosyl, xylosyl, or arabinosyl, and the corresponding compounds can be obtained through reacting the orcinol with the indicated acetylated product of sugars in methanol under light-protection and by addition of hydrobromic acid and acetic acid and stirring for 1-5 h at room temperature. Orcinol acetylated glycosides are obtained. The corresponding orcinol acetylated glycosides are treated with sodium methoxide in methanol for 1-5 h at room temperature to give the corresponding orcinol glycosides.

2. When $R^1$ and $R^2$ are acyl, orcinol or orcinol glycosides are dissolved in pyridine by the addition of the corresponding acid anhydrides or acyl chlorides and 10-20% 4-dimethylaminopyridine and stirring for 3-5 h at 60-120° C. The mixture is poured onto water and then extracted with chloroform to give a crude product which is further purified to give acylated products.

3. When $R^1$ and $R^2$ are alkyl, orcinol or orcinol glycosides are dissolved in tetrahydrofuran or dimethyl sulfoxide by addition of sodium hydride and stirring for 30-60 min. After addition of the corresponding alkylogen, the reaction mixture is further stirred for 3-5 h, and then poured into water and extracted with chloroform to give a crude product which is further purified to give alkylated products.

EXAMPLE 1

Extraction and isolation of orcinol-1-O-β-D-glucopyranoside, orcinol, and orcinol-1-O-[β-D-glucopyranosyl-(1→6)]-β-D-glucopyranoside Curculigo orchioides Garr. was collected, dried in the shade or in the sun, and powdered.

The powdered material (20 kg) was extracted 3 times with 90% ethanol (200 kg) under reflux for 2 h each time. The extracts were combined and concentrated to about 30 kg, and filtered after 12 h deposition. The crude extracts were then chromatographed on a D-101 macroporous resin column (the weight of the resin was 20 kg) and eluted successively with 100 kg distilled water, 60 kg 70% ethanol, and 60 kg 90% ethanol. The 70% ethanol eluent and the 90% ethanol eluent were separately collected and evaporated to dryness to obtain 70% ethanol eluent (340 g) and 90% ethanol eluent (60 g).

The obtained 70% ethanol eluent (340 g) was dissolved in methanol and absorbed in 400 g of silica gel. After being dried at room temperature, the solid was pulverized and sieved and subjected to silica gel column chromatography (2.1 kg, 200-300 mesh) and eluted with chloroform-methanol-water (90:10:1 to 70:30:3, v/v/v) to obtain 26 fractions. Each fraction was 1500 ml. Fractions 2-3 were combined, concentrated, and crystallized from ethanol to give orcinol (5 g). Fractions 9-15 were combined, concentrated, and crystallized from ethanol to give orcinol-1-O-β-D-glucopyranoside (50 g). Fractions 22-26 were combined, concentrated and crystallized from ethanol to give orcinol-1-O-[β-D-glucopyranosyl-(1-6)]-β-D-glucopyranoside (10 g).

Structure determination: The optical rotation was measured with a SEPA-300 polarimeter; UV-VIS spectra were obtained with a UV-210A spectrometer; IR data were collected on a Bio-Rad FTS-135 spectrometer with KBr pellets; nuclear magnetic resonance ($^1$H NMR and $^{13}$C NMR) spectra were run on a Bruker DRX500 spectrometer in $CDCl_3$ with TMS as internal standard. Materials for column chromatography and thin-layer chromatography silica gel were from Makall Group Co. Ltd. (Qingdao, China).

Name: Orcinol-1-O-β-D-glycopyranoside

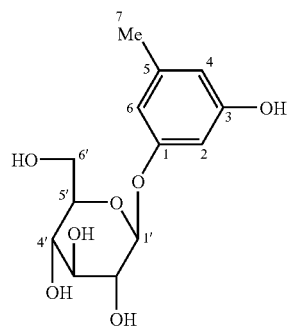

Molecular formula: $C_{13}H_{18}O_7$;
Molecular weight: 286;
Properties: Light yellow powder;
$[\alpha]_D$ −63.03° (c 5.95, methanol);
UV (methanol): $\lambda_{max}$ (log ε) 279 (3.19), 273 (3.21), 219 (3.99), 203 (4.58);
IR (KBr): $\upsilon_{max}$ 3495, 3385, 1620, 1596, 1175, 1076, 1032 $cm^{-1}$; FAB-MS (−): m/z 285 [(M−1)$^-$, 100], 123 [(M−1-glc)$^-$, 87];
$^1$H-NMR (CD$_3$OD, 400 MHz) $\delta_H$: 6.41 (1H, s, H-2), 6.36 (1H, s, H-6), 6.29 (1H, s, H-4), 4.84 (1H, d, J=7.3 Hz, H-1'), 2.22 (3H, s, H-7);
$^{13}$C-NMR (CD$_3$OD, 100 MHz) $\delta_C$: 160.1 (s, C-1), 111.4 (d, C-2), 159.2 (s, C-3), 102.4 (s, C-4), 141.3 (s, C-5), 110.0 (d, C-6), 21.6 (q, C-7), 102.5 (d, C-1'), 75.0 (d, C-2'), 78.1 (d, C-3'), 71.6 (d, C-4'), 78.2 (d, C-5'), 62.7 (t, C-6').

Name: Orcinol

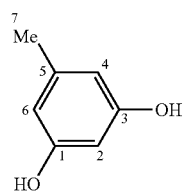

Molecular formula: $C_7H_8O_2$;
Molecular weight: 124;
Properties: Light yellow-white powder;
UV (methanol): $\lambda_{max}$ (log ε) 281 (3.20), 275 (3.22), 204 (4.59);
IR (KBr): $\upsilon_{max}$ 3313, 1629, 1601, 1512, 1477, 1332, 1208, 1148, 1032, 973 $cm^{-1}$;
EI-MS (70 ev): m/z 125 [(M+1)$^+$, 8], 124 [M$^+$, 100], 123 [(M−1)$^+$, 55], 107[(M+1−18)$^+$, 7], 95 (12), 77(8);
$^1$H-NMR (CD$_3$OD, 400 MHz) $\delta_H$: 6.14 (2H, brs, H-2,6), 6.10 (1H, brs, H-4), 2.16 (3H, s, H-7);

$^{13}$C-NMR (CD$_3$OD, 100 MHz) δ$_C$: 159.2 (s×2, C-1, 3), 108.7 (d×2, C-2, 6), 108.7 (s, C-4), 141.2 (s, C-5), 21.5 (q, C-7).

Name: Orcinol-1-O-[β-D-glucopyranosyl-(1-6)]-β-D-glucopyranoside

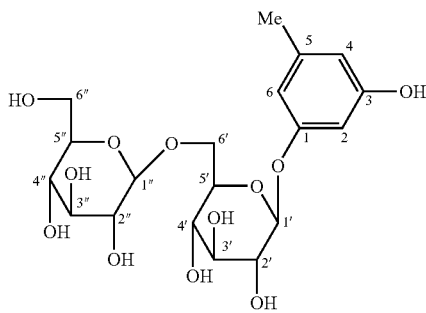

Molecular formula: C$_{19}$H$_{28}$O$_{12}$;
Molecular weight: 448;
Properties: White amorphous powder;
M.p.: 117-119° C.;
FAB-MS (−) (m/z): 447 [M−1]$^−$, 123 [M−1-2glc];
$^1$H NMR (400 MHz, CD$_3$OD) δ$_H$: 6.43 (1H, brs, H-2), 6.40 (1H, brs, H-4), 6.28 (1H, brs, H-6), 4.82 (1H, d, J=7.30 Hz, H-1'), 4.40 (1H, d, J=7.73 Hz, H-1"), 2.21 (3H, s, H-7);
$^{13}$C NMR (125 MHz, CD$_3$OD) δ$_C$: 160.0 (s, C-1), 102.0 (d, C-2), 159.2 (s, C-3), 111.2 (d, C-4), 141.3 (s, C-5), 109.8 (d, C-6), 21.7 (s, C-7), 102.1 (d, C-1'), 74.8 (d, C-2'), 77.7 (d, C-3'), 71.3 (s, C-4'), 77.5 (d, C-5), 69.6 (t, C-6'), 104.6 (d, C-1"), 75.2 (d, C-2"), 77.8 (d, C-3"), 71.5 (d, C-4"), 77.9 (d, C-5"), 62.6 (t, C-6").

EXAMPLE 2

Preparation of 1,3-O-diacetylorcinol

A 100 ml round-bottomed flask was charged with pyridine (40 ml) and orcinol (1.24 g, 0.01 mol). The reaction mixture was stirred at room temperature and acetic anhydride (3 ml) was added dropwise. After being stirred for 24 h at room temperature, the reaction mixture was poured into 200 ml of ice water. The mixture was extracted with ethyl acetate (3×50 ml). The organic layers were combined, washed 3 times with 5% hydrochloric acid, 3 times with saturated NaHCO$_3$ aq., and 3 times with saturated sodium chloride, dried over Na$_2$SO$_4$, filtered, and evaporated to dryness under vacuum. The crude product was subjected to silica gel column chromatography and eluted with petroleum ether-acetone (90:10, v/v) to give 1,3-O-diacetylorcinol (1.87 g, yield 90%).

Name: 1,3-O-Diacetylorcinol

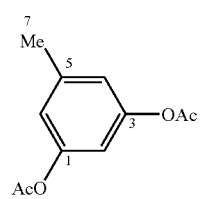

Molecular formula: C$_{11}$H$_{12}$O$_4$;
Molecular weight: 208;
Properties: Colorless oil Structural data of 1,3-O-Diacetylorcinol:
ESI-MS (+) m/z: 231 [M+Na]$^+$;
IR (KBr) ν$_{max}$: 1769, 1602, 1592, 1466, 1434, 1369, 1292, 1198, 1124, 1036 cm$^{-1}$;
$^1$H NMR (CDCl$_3$) δ$_H$: 6.78 (2H, s, J=1.9 Hz, H-4, 6), 6.71 (1H, d, J=1.9 Hz, H-2), 2.30 (3H, s, H-7), 2.19 (s, 6H);
$^{13}$C NMR (CDCl$_3$) δ$_C$: 169.0 (s, CH$_3$CO), 169.0 (s, CH$_3$CO), 150.9 (s, C-1), 150.9 (s, C-3), 140.3 (s, C-5), 119.7 (d, C-4), 119.7 (d, C-6), 112.5 (d, C-2), 21.2 (q, C-7), 20.9 (q, CH$_3$CO), 20.9 (q, CH$_3$CO).

EXAMPLE 3

Preparation of 3-O-acetyl-orcinol-1-O-(2,3,4,6-tetraacetyl)-β-D-glucopyranoside

Orcinol (286 mg) was dissolved in pyridine (20 ml). The reaction mixture was stirred at room temperature and acetic anhydride (2.5 g, 25 mmol) was added dropwise. After being stirred for 24 h at room temperature, the reaction mixture was poured into 50 ml of ice water. The mixture was extracted with ethyl acetate (3×20 ml). The organic layers were combined, washed 3 times with 5% hydrochloric acid, 3 times with saturated NaHCO$_3$ aq., and 3 times with saturated sodium chloride, dried over Na$_2$SO$_4$, filtered, and evaporated to dryness under vacuum. The crude product was subjected to silica gel column chromatography to give 3-O-acetyl-orcinol-1-O-(2,3,4,6-tetraacetyl)-β-D-glucopyranoside (421 mg, yield 85%).

Name: 3-O-Acetyl-orcinol-1-O-(2,3,4,6-tetraacetyl)-β-D-glucopyranoside

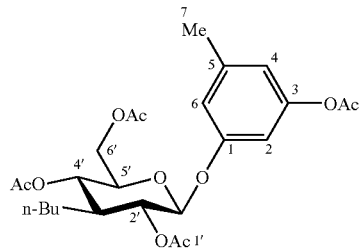

Molecular formula: C$_{23}$H$_{28}$O$_{12}$;
Molecular weight: 496;
Properties: White amorphous powder;
ESI-MS (+) m/z: 519 [M+Na]$^+$;
IR (KBr) ν$_{max}$: 1759, 1625, 1590, 1373, 1241, 1211 cm$^{-1}$;
$^1$H NMR (CDCl$_3$) δ$_H$: 6.68 (1H, s, J=1.9 Hz), 6.63 (1H, s, J=1.9 Hz), 6.54 (1H, s, J=1.9 Hz), 5.30-5.22 (m, 2H), 5.14 (t, 1H, J=9.7 Hz), 5.06 (1H, d, J=7.5 Hz), 4.28-4.14 (m, 2H), 3.89-3.85 (m, 1H), 2.31 (s, 3H), 2.27 (s, 3H), 2.08 (s, 3H), 2.05 (s, 3H), 2.04 (s, 3H), 2.03 (s, 3H);
$^{13}$C NMR (CDCl$_3$) δ$_C$: 170.6 (s, CH$_3$CO), 170.2 (s, CH$_3$CO), 169.4 (s, CH$_3$CO), 169.3 (s, CH$_3$CO), 169.3 (s, CH$_3$CO), 157.2 (s, C-3), 151.1 (s, C-1), 140.6 (s, C-5), 117.2 (d, C-6), 115.1 (d, C-4), 107.6 (d, C-2), 98.8 (s, C-1'), 72.6 (d, C-3'), 72.0 (d, C-5'), 71.0 (d, C-2'), 68.2 (d, C-4'), 62.0 (t, C-6'), 21.5 (q, C-7), 21.1 (q, CH$_3$CO), 20.6 (q, CH$_3$CO×4).

EXAMPLE 4

Preparation of orcinol-1-tetra-O-acetyl-rhamnopyranose

Tetra-O-acetyl-rhamnopyranose (36 g) was dissolved in a mixture (100 ml) of hydrobromic acid and acetic acid. The reaction mixture was stirred for 5 h under light-protection. The reaction mixture was poured into 500 ml of ice water and extracted with ethyl acetate (3×500 ml). The organic layers were combined, washed 3 times with water, 3 times with 5% NaHCO$_3$ aq., and 3 times with saturated sodium chloride, dried over Na$_2$SO$_4$, filtered, and evaporated to dryness under vacuum to give tetra-O-acetyl-rhamnopyranosyl bromide.

Orcinol (12.4 g) was dissolved in chloroform (20 ml). The reaction mixture was stirred and 5% sodium hydroxide solution (20 ml) was added. When the temperature was raised to 50° C., solution of the tetra-O-acetyl-rhamnopyranosyl bromide (0.12 mol) dissolved in chloroform was added dropwise. The reaction mixture was stirred at 50° C. until the reaction was completed, then poured into 150 ml of ice water. The pH was adjusted to 7 with 5% hydrochloric acid. The mixture was extracted with ethyl acetate. The organic layers were combined, washed with saturated sodium chloride, dried over Na$_2$SO$_4$, filtered, and evaporated to dryness under vacuum. The crude product was subjected to silica gel column chromatography and eluted with ethyl acetate-petroleum ether (5:1, v/v) to give orcinol-1-tetra-O-acetyl-rhamnopyranose (1.87 g, yield 90%).

EXAMPLE 5

Preparation of orcinol-1-rhamnopyranose

Sodium methoxide (0.18 g) was added to a solution of orcinol-1-tetra-O-acetyl-rhamnopyranose (4.14 g) in methanol (20 ml). After being stirred for 2 h at room temperature, the reaction mixture was neutralized with 5% hydrochloric acid. The methanol was removed under vacuum after addition of distilled water (50 ml). The mixture was extracted with n-butanol (3×50 ml). The organic layers were combined, washed with saturated sodium chloride, dried over Na$_2$SO$_4$, filtered, and evaporated to dryness under vacuum. The crude product was crystallized from ethanol to give orcinol-1-rhamnopyranose.

EXAMPLE 6

Orcinol-1-O-β-D-glycopyranoside prepared according to EXAMPLE 1 was dissolved in water for injection. After bacterial filtration (0.2-0.45 μm filtration), the solution was sub-packaged into vials, sealed, and sterilized to give injection of orcinol-1-O-β-D-glycopyranoside.

EXAMPLE 7

Orcinol-1-O-β-D-glycopyranoside prepared according to EXAMPLE 1 was dissolved in bacteria-free water for injection. The solution was filtered by vacuum filtration using a Buchner funnel, filtered with a precision filter (0.2-0.45 μm filtration) under bacteria-free conditions, sub-packaged into ampoules, and sealed after lyophilization to give lyophilized powder for injection of orcinol-1-O-β-D-glycopyranoside.

EXAMPLE 8

Orcinol-1-O-β-D-glycopyranoside prepared according to EXAMPLE 1 was mixed with excipients to give powder injection of orcinol-1-O-β-D-glycopyranoside. The weight ratio of the former to the latter was 9:1.

EXAMPLE 9

Orcinol-1-O-β-D-glycopyranoside was prepared according to EXAMPLE 1. Tablets, capsules, and granules were prepared by mixing orcinol-1-O-β-D-glycopyranoside with excipients in weight ratios of the compound and excipients between 1:5 and 1:10.

EXAMPLE 10

Orcinol-1-O-β-D-glycopyranoside was prepared according to EXAMPLE 1. Oral liquid of orcinol-1-O-β-D-glycopyranoside was prepared according to conventional methods.

EXAMPLE 11

Orcinol-1-O-β-D-glycopyranoside was prepared according to EXAMPLE 1. Capsules and granules were prepared by mixing orcinol-1-O-β-D-glycopyranoside with excipients in a weight ratio of 5:1.

EXAMPLE 12

Orcinol-1-O-β-D-glycopyranoside (12.4 g) prepared according to EXAMPLE 1, starch (600 g), lactose (200 g), menthol (5 g) and sodium carboxymethyl starch (183 g) were mixed and further prepared to be troches as functional foods.

For a better understanding of the essence of the invention, the pharmacological effects of pharmaceutical compositions containing orcinol or its derivatives and pharmaceutical carriers or excipients were studied. However, it is to be understood that the present invention is not limited to the specific details described.

EXPERIMENT 1

Pharmacological Study of ORG and OR

1 Antidepressant Effects of ORG and OR with Dose-Effect Relationship in the Tail Suspension Test (TST) and Forced Swim Test (FST) in Rats and Mice
1.1 Experimental Methods Kunming mice and Sprague-Dawley rats (Certificate Number: A4CXK(Chuan)2003-16) from the Institute of Experimental Animals, People's Hospital of Sichuan Province, were used. The mice were 3-4 weeks old at the beginning of experiments and weighed 25-30 g. The rats weighed 250-300 g. The numbers of animals in each group are shown in Tables 1-5. Orcinol (OR), orcinol-1-O-β-D-glucopyranoside (ORG), orcinol-1-O-[β-D-glucopyranosyl-(1→6)]-β-D-glucopyranoside (ORGG), 1,3-O-diacetylorcinol (OR-2Ac), and 3-O-acetyl-orcinol-1-O-(2,3,4,6-tetraacetyl)-β-D-glucopyranoside (ORG-5Ac) were prepared according to Examples 1, 2, and 3. Animals were divided into an experimental group with different doses, a vehicle group, and two positive control groups containing an imipramine group (Sigma, Batch No. 106k1588) and a venlafaxine group (Wuhan Yuancheng Co., Ltd., Batch No. 200701001).

Drugs: ORG was dissolved in normal saline. In positive controls, imipramine or venlafaxine was suspended in normal saline containing 0.5 CMC-sodium by sonication. The dose of imipramine or venlafaxine was 15 mg/kg. The i.g. or i.p. injection volume was 0.1 ml/10 g in mice and 1 ml/100 g or 0.1 ml/100 g in rats.

FST in mice: The apparatus consisted of a cylinder (24 cm high×15 cm diameter) filled with water to 17 cm deep, at a temperature of 24±2° C. All drugs and vehicles were administered 24 h and 5 h before the FST started. The immobility time of mice during the last 4 min of the total 6-min period was recorded manually.

FST in rats: There were two swim sessions in each experiment. First, a pre-test swim session for 15 min was performed and the immobility time during the first 5-min periods was recorded manually. If the immobility time was too long or too short, the rat was rejected. All drugs and vehicles were administered twice at 0 and 19 h after the pre-test swim session. Twenty-four hours after the pre-test swim session, the immobility time during the 5-min test session was recorded manually.

TST in mice: All drugs and vehicles were administered 24 h and 5 h before the TST started. Mice were suspended by a adhesive tape to attach their tails at 2 cm of the tail tip to a horizontal bar that was placed 50 cm above the floor of the testing chamber. The immobility time during 6 min was recorded manually.

Data analysis: The results are expressed as mean±SEM and were analyzed using SPSS 11 software. Comparisons between groups were made using one-way analyses of variance (ANOVA) followed by the least significant difference (LSD) test. The significance level was set at P<0.05. The $ED_{50}$ values were calculated using GraphPad Prism software.

1.2 Results 1.2.1 Antidepressant Effect of ORG (i.g.) on FST in Rats

TABLE 1

Dose-immobility time relationship of ORG (i.g.) in FST in rats

| Group | Dose (mg/kg) | Number of animals | Immobility time (s) (mean ± SEM) | P value |
|---|---|---|---|---|
| NS | 1 ml/100 g | 30 | 179.50 ± 5.32 | |
| ORG | 0.0625 | 10 | 187.20 ± 11.97 | 0.60 |
| | 0.125 | 20 | 181.50 ± 8.19 | 0.86 |
| | 0.1875 | 20 | 138.90 ± 13.31* | 0.006 |
| | 0.25 | 20 | 121.05 ± 9.44* | <0.001 |
| | 0.5 | 20 | 113.70 ± 6.74* | <0.001 |
| | 1 | 20 | 96.87 ± 7.40* | <0.001 |
| | 2 | 20 | 91.60 ± 7.06* | <0.001 |
| | 4 | 20 | 84.40 ± 9.20* | <0.001 |
| | 8 | 20 | 94.30 ± 9.86* | <0.001 |
| | 16 | 20 | 91.40 ± 11.36* | <0.001 |
| | 32 | 19 | 107.26 ± 10.74* | <0.001 |
| | 64 | 20 | 105.90 ± 19.77* | <0.001 |
| | 128 | 20 | 103.00 ± 17.42* | <0.001 |
| Venlafaxine | 15 | 10 | 100.80 ± 9.84* | <0.001 |
| Imipramine | 15 | 29 | 92.72 ± 7.09* | <0.001 |

*P < 0.05 (one way ANOVA followed by LSD).

The dose-effect relationship of ORG administered orally in rats was evaluated. ORG decreased the immobility time and the effect was significantly dependent on the dose (Table 1). The dose of the best efficacy was 4 mg/kg, and the $ED_{50}$ was about 0.22 mg/kg.

1.2.2 Antidepressant Effect of ORG (i.g.) on FST in Mice

In the present study, ORG was administered i.g. at 24 h and 5 h before the FST started. The immobility time decreased and the effect was significantly dependent on the dose (Table 2). The dose of the best efficacy was 3 mg/kg, and the $ED_{50}$ was about 0.22 mg/kg.

TABLE 2

Dose-immobility time relationship of ORG (i.g.) in FST in mice

| Group | Dose (mg/kg) | Number of animals | Immobility time (s) (mean ± SEM) | P value |
|---|---|---|---|---|
| NS | 0.1 ml/10 g | 108 | 178.50 ± 3.04 | |
| ORG | 0.093 | 40 | 169.35 ± 4.32 | 0.26 |
| | 0.186 | 30 | 155.30 ± 9.19* | 0.01 |
| | 0.3725 | 30 | 137.57 ± 6.41* | <0.001 |

TABLE 2-continued

Dose-immobility time relationship of ORG (i.g.) in FST in mice

| Group | Dose (mg/kg) | Number of animals | Immobility time (s) (mean ± SEM) | P value |
|---|---|---|---|---|
| | 0.75 | 60 | 139.45 ± 7.04* | <0.001 |
| | 1.5 | 60 | 127.23 ± 6.63* | <0.001 |
| | 3 | 78 | 114.41 ± 6.23* | <0.001 |
| | 6 | 70 | 129.76 ± 5.99* | <0.001 |
| | 12 | 70 | 122.71 ± 5.56* | <0.001 |
| | 24 | 70 | 121.57 ± 6.13* | <0.001 |
| | 48 | 69 | 135.36 ± 4.60* | <0.001 |
| | 96 | 50 | 145.34 ± 5.39* | <0.001 |
| Venlafaxine | 15 | 78 | 134.28 ± 3.76* | <0.001 |
| Imipramine | 15 | 79 | 131.20 ± 3.91* | <0.001 |

*P < 0.05 (one way ANOVA followed by LSD).

1.2.3 Antidepressant Effect of ORG (i.g.) on TST in Mice

ORG was administered i.g. at 24 h and 5 h before the TST started. The immobility time decreased and the effect was significantly dependent on the dose (Table 3). The dose of the best efficacy was 12 mg/kg, and the $ED_{50}$ was about 0.73 mg/kg.

TABLE 3

Dose-immobility time relationship of ORG (i.g.) in TST in mice

| Group | Dose (mg/kg) | Number of animals | Immobility time (s) (mean ± SEM) | P value |
|---|---|---|---|---|
| NS | 0.1 ml/10 g | 38 | 161.18 ± 5.47 | |
| ORG | 0.1875 | 40 | 161.70 ± 6.89 | 0.95 |
| | 0.375 | 40 | 155.68 ± 6.77 | 0.52 |
| | 0.5 | 30 | 125.30 ± 6.93* | <0.001 |
| | 0.75 | 30 | 117.33 ± 6.56* | <0.001 |
| | 1.5 | 30 | 109.27 ± 6.81* | <0.001 |
| | 3 | 30 | 98.07 ± 5.95* | <0.001 |
| | 6 | 30 | 89.73 ± 5.02* | <0.001 |
| | 12 | 30 | 77.67 ± 5.33* | <0.001 |
| | 24 | 30 | 91.03 ± 7.44* | <0.001 |
| | 48 | 20 | 100.20 ± 10.46* | <0.001 |
| | 96 | 19 | 107.68 ± 8.85* | <0.001 |
| Venlafaxine | 15 | 20 | 102.85 ± 9.34* | <0.001 |
| Imipramine | 15 | 40 | 105.65 ± 5.71* | <0.001 |

*P < 0.05 (one way ANOVA followed by LSD)

1.2.4 Antidepressant Effect of OR (i.p.) on FST in Mice

In this study, OR was administered i.p. at 24 h and 5 h before the FST started. The immobility time decreased (Table 4).

TABLE 4

Effect of OR (i.p.) on immobility time in FST in mice

| Group | Dose (mg/kg) | Number of animals | Immobility time (s) (mean ± SEM) | P value |
|---|---|---|---|---|
| NS | 0.1 ml/10 g | 9 | 156.56 ± 19.78 | |
| OR | 10 | 10 | 82.40 ± 10.64* | 0.005 |
| Imipramine | 15 | 13 | 96.38 ± 12.04 | 0.15 |

*P < 0.05 (one way ANOVA followed by LSD)

1.2.5 Antidepressant Effect of the Derivatives of ORG (i.p.) on FST in Mice

In this study, the derivatives of ORG (ORGG, OR-2Ac, and ORG-5Ac) were administered by intraperitoneal (i.p.) injection at 24 h and 5 h before the FST started. All derivatives of ORG decreased the immobility time of mice in the FST model (Table 5).

TABLE 5

Effect of derivatives of ORG (i.p.) on immobility time in FST in mice

| Group | Dose (mg/kg) | Number of animals | Immobility time (s) (mean ± SEM) | P value |
|---|---|---|---|---|
| NS | 0.1 ml/10 g | 10 | 213.60 ± 3.77 | |
| ORGG | 10 | 10 | 184.20 ± 11.29* | 0.012 |
| OR-2Ac | 10 | 10 | 170.10 ± 6.37* | <0.001 |
| ORG-5Ac | 10 | 10 | 178.90 ± 9.61* | 0.003 |
| Imipramine | 15 | 10 | 146.00 ± 6.46* | <0.001 |

*$P < 0.05$ (one way ANOVA followed by LSD)

1.3 Therapeutic Index (TI) of Antidepressant Activity of ORG

In the acute toxicity test, when Kunming mice were administered ORG at a dose of 1750 mg/kg, the saturated concentration, ethological and histological investigation found nothing abnormal. So the median toxic dose ($TD_{50}$) of ORG was higher than 1750 mg/kg.

The therapeutic index (TI) of ORG in mice in FST=$TD_{50} \div ED_{50}$=>1750 mg/kg=0.22 mg/kg=>7955.

The therapeutic index (TI) of ORG in mice in TST=$TD_{50} \div ED_{50}$=>1750 mg/kg=0.73 mg/kg=>2397.

EXPERIMENT 2

Antidepressant Effect of ORG with Time Course-Dependence in Forced Swim Test (FST) in Mice 2.1 Experimental Methods Kunming mice (Certificate Number: A4CXK(Chuan) 2003-16) from the Institute of Experimental Animals, People's Hospital of Sichuan Province, were used. They were 3-4 weeks old at the beginning of the experiments and weighed 25-30 g. The numbers of animals in each group are shown in Tables 6-8. ORG was prepared as described in Example 1. Animals were divided into experiment groups with different doses and vehicle control groups.

2.1.1 Administration and Experimental Design:

ORG was dissolved in normal saline (NS) at different concentrations. All drugs and their vehicles were administered orally in a volume of 0.1 ml/10 g.

2.1.2 Frequency of administration:

Animals were treated with ORG (3 mg/kg) or NS 1 to 5 times orally within 24 h. The immobility time was recorded 5 h after the last ORG treatment.

2.1.3 Comparison of Different Doses and Frequencies of Administration:

Mice were treated once with 6 mg/kg ORG or twice with 3 mg/kg ORG within 24 h. The immobility time was recorded 5 h after the last ORG treatment.

2.1.4 Effect of ORG on Antidepressant Activity (Onset Time and Maintenance Time):

Mice were treated with ORG (3 mg/kg). Nineteen hours after administration, another dose of ORG (3 mg/kg) was given.

The immobility time was recorded at 2.5 h, 5 h, 24 h, 72 h and 2 weeks after the second administration.

2.1.5 Data Analysis:

The results are expressed as mean±SEM (%). The immobility times of the NS groups were set as 100%, and the antidepressant effect of each group was calculated based on the NS group. A better antidepressant effect is shown as a lower percentage value. This normalization method permitted comparisons among the experimental groups. Statistic analysis was one-way ANOVA followed by the LSD test. A value of $P<0.05$ was considered significant.

2.2. Results 2.2.1 Antidepressant Effect of ORG at Different Frequencies of Administration Within 24 h on FST in Mice.

ORG (3 mg/kg) was administered 1-5 times within 24 h. The immobility time decreased significantly in the groups treated 2 or 3 times with ORG (Table 6). The results show that the best drug effect was obtained after 2 or 3 times of administration within 24 h at intervals of 10-19 h.

TABLE 6

Frequency of administration and antidepressant effect of ORG on FST in mice

| Group | Dose (mg/kg) | Frequency of administration in 24 h | Numbers of animals | Immobility (% NS) (mean ± SEM) | P Value |
|---|---|---|---|---|---|
| NS | | | 10 | 100 | |
| ORG | 3 | 1 | 10 | 83.57 ± 6.66 | 0.098 |
| | 3 | 2 | 10 | 64.98 ± 5.96* | 0.001 |
| | 3 | 3 | 10 | 65.65 ± 9.67* | 0.001 |
| | 3 | 4 | 10 | 89.81 ± 6.50 | 0.302 |
| | 3 | 5 | 10 | 91.26 ± 5.93 | 0.375 |

*$P < 0.05$ (one way ANOVA followed by LSD)

2.2.2 Comparison of Antidepressant Effect Among Different Frequencies of Administration with the Same Final Dose Within 24 h When mice were treated once with 6 mg/kg ORG or twice with 3 mg/kg ORG in 24 h, the immobility times decreased in all groups (Table 7). But a better effect was shown in mice treated twice with 3 mg/kg ORG in 24 h.

TABLE 7

The same dose administered twice had a better antidepressant effect than when administered once within 24 h

| Group | Dose (mg/kg) | Frequency of administration in 24 h | Number of animals | Immobility (% NS) (mean ± SEM) | P value |
|---|---|---|---|---|---|
| NS | | | 31 | 100 | |
| ORG | 3 | 2 | 9 | 64.03 ± 7.20* | <0.001 |
| ORG | 6 | 1 | 30 | 80.70 ± 4.64* | =0.002 |

*$P < 0.05$ (one way ANOVA followed by LSD)

2.2.3 Antidepressant Effect of ORG with Fast Onset and Long-Lasting Maintenance in FST Mice were given ORG orally (3 mg/kg). Nineteen hours later, another dose of ORG (3 mg/kg) was given. The immobility time was recorded at 2.5 h, 5 h, 24 h, 72 h and 2 weeks after the second administration. The antidepressant effect of ORG occurred rapidly at 2.5 h after the second administration. The best effect occurred at 24 h after the second administration and the effect was maintained for at least 72 h (Table 8). The results show that ORG has a fast onset of antidepressant effect that lasts for at least 72 h.

TABLE 8

Time-response relationship for ORG in FST in mice

| Group | Dose (mg/kg) | Time after last administration (h) | Number of animals | Immobility (% NS) (mean ± SEM) | P value |
|---|---|---|---|---|---|
| NS | | | 50 | 100 | |
| ORG | 6 | 2.5 | 20 | 73.63 ± 4.21* | <0.001 |
| | 6 | 5 | 20 | 71.92 ± 6.05* | 0.001 |
| | 6 | 24 | 20 | 62.83 ± 6.59* | <0.001 |
| | 6 | 72 | 20 | 77.33 ± 6.07* | 0.002 |
| | 6 | 2 (weeks) | 20 | 99.54 ± 5.54 | 0.954 |

*$P < 0.05$ (one way ANOVA followed by LSD)

EXPERIMENT 3

Antidepressant Effect of ORG in the Chronic Unpredictable Mild Stress Model in Mice Chronic unpredictable mild stress (CMS) is considered to be a depression model that has the same etiology of chronic stress that exacerbates or causes depression in humans. A variety of unpredictable mild stresses such as drink or food restriction, restraint, and swimming, may lead animals to a lack of response to reward (e.g. sugar drink preference). Immobility time is significantly increased in the FST and TST after CMS exposure, indicating more severe depression. Thus, CMS is widely used to evaluate the effects of antidepressants on depression caused by stress.

3.1. Experimental Methods

Kunming mice (Certificate Number: A4CXK(Chuan) 2003-16) from the Institute of Experimental Animals, People's Hospital of Sichuan Province, were used. They were 3-4 weeks old at the beginning of experiments and weighed 25-30 g. The numbers of animals in each group are shown in Tables 9 and 10. ORG was prepared as described in Example 1. Animals were divided into experiment groups with different doses, a vehicle control group, and an imipramine group (Sigma, Batch No. 106k1588) as positive control.

CMS model: The chronic mild stresses that Kunming mice were subjected to were reversal of circadian rhythm, continuous light, cold, damp bedding, tilt cages, food and water restriction, and restraint. Only one of these stresses was given to each mouse randomly within 24 h, and the same stress did not appear twice consecutively. The stress period lasted for 8 weeks. In the last week, ORG was administered orally once a day for 7 consecutive days. The behavioral test was carried out 30 min after the last administration. The parameter tested was immobility time in the FST and TST in the CMS model mice. The methods of FST and TST and data analysis were as described above.

3.2. Results 3.2.1 Antidepressant Effect of ORG in FST in CMS Model Mice

ORG significantly decreased the immobility time in the FST, and the effects were significantly dependent on dose (Table 9). The best dose for the antidepressant effect was 20 mg/kg, and the $ED_{50}$ was 0.81 mg/kg.

TABLE 9

Dose-immobility time relationship of ORG in FST in CMS model mice

| Group | Dose (mg/kg) | Number of animals | Immobility time (s) (mean ± SEM) | P value |
|---|---|---|---|---|
| NS | 0.1 ml/10 g | 28 | 208.00 ± 5.57 | |
| ORG | 1.25 | 10 | 190.90 ± 12.94 | 0.255 |
| | 2.5 | 11 | 177.00 ± 11.78* | 0.033 |
| | 5 | 10 | 177.50 ± 12.39* | 0.043 |
| | 10 | 19 | 170.84 ± 10.48* | 0.002 |
| | 20 | 20 | 164.95 ± 11.36* | <0.001 |
| Imipramine | 15 | 10 | 166.00 ± 13.84* | 0.005 |

*$P < 0.05$ (one way ANOVA followed by LSD)

3.2.2 Antidepressant Effect of ORG in TST in CMS Model Mice

ORG significantly decreased the immobility time in the TST, and the effects were significantly dependent on dose (Table 10). The best dose for the antidepressant effect was 20 mg/kg, and the $ED_{50}$ was about 4.22 mg/kg.

TABLE 10

Dose-immobility time relationship of ORG in TST in CMS model mice

| Group | Dose (mg/kg) | Number of animals | Immobility time (s) (mean ± SEM) | P value |
|---|---|---|---|---|
| NS | 0.1 ml/10 g | 16 | 185.25 ± 6.66 | |
| ORG | 1.25 | 10 | 171.20 ± 13.02 | 0.392 |
| | 5 | 10 | 146.30 ± 11.66* | 0.018 |
| | 10 | 16 | 145.31 ± 12.41* | 0.006 |
| | 20 | 16 | 140.69 ± 14.14* | 0.002 |
| Imipramine | 15 | 9 | 131.22 ± 10.61* | 0.002 |

*$P < 0.05$ (one way ANOVA followed by LSD)

3.3 TI of ORG in TST and FST in CMS Model Mice

In the acute toxicity testing, when the mice were administered ORG at a dose of 1750 mg/kg, the saturated concentration, ethological and histological investigation did not find abnormalities. So the median toxic dose ($TD_{50}$) of ORG was higher than 1750 mg/kg.

The therapeutic index (TI) of ORG in CMS mice in FST=>1750 mg/kg÷0.81 mg/kg=>2160. The therapeutic index (TI) of ORG in CMS mice in TST=$TD_{50}$÷$ED_{50}$=>1750 mg/kg÷4.22 mg/kg=>415.

EXPERIMENT 4

Antidepressant Effect of ORG in the Constant Darkness (DD) Model in Mice

The DD model is an etiological model reported recently that is used to study depression associated with circadian rhythm disorder. In this model, the animal's circadian rhythm is changed in a continuous dark-rearing condition that induces or exacerbates depression. So in this study, the DD model was used to cause or exacerbate depression and the antidepressant effect of ORG was then tested in FST and TST.

4.1 Experimental Methods

Kunming mice (Certificate Number: A4CXK(Chuan) 2003-16) from the Institute of Experimental Animals, People's Hospital of Sichuan Province, were used. They were 3-4 weeks old at the beginning of the experiments and weighed 25-30 g. Numbers of animals in each group are shown in Tables 11 and 12. ORG was prepared as described in Example 1. Animals were divided into experimental groups with different doses, vehicle control groups, and an imipramine group (Sigma, Batch No. 106k1588) as positive control.

DD model in mice: Mice were kept under 24 h continuous dark conditions. The replacement of padding, addition of food and water, and other operations were undertaken in the condition that the intensity of red light was less than 1.0 lux. The period of this condition lasted for 28 days. In the last week, ORG was administered orally once a day for 1 week. The FST and TST were carried out 30 min after the last administration. Methods and data analysis were as described above.

4.2 Results 4.2.1 Antidepressant Effect of ORG in FST in DD Model Mice

ORG significantly decreased the immobility time in the FST, and the effects were significantly dependent on the dose (Table 11). The dose of the best efficacy was 10 mg/kg, and the $ED_{50}$ was about 1.48 mg/kg.

TABLE 11

Dose-immobility time relationship of ORG in FST in DD model mice

| Group | Dose (mg/kg) | Number of animals | Immobility time (s) (mean ± SEM) | P value |
|---|---|---|---|---|
| NS | 0.1 ml/10 g | 32 | 193.13 ± 5.57 | |
| ORG | 1.25 | 11 | 180.27 ± 10.36 | 0.306 |
| | 2.5 | 11 | 174.27 ± 11.89 | 0.134 |
| | 5 | 10 | 161.70 ± 14.89* | 0.016 |
| | 10 | 21 | 151.86 ± 8.89* | <0.001 |
| | 40 | 10 | 156.60 ± 13.86* | 0.005 |
| Imipramine | 15 | 11 | 161.22 ± 13.08* | 0.019 |

*P < 0.05 (one way ANOVA followed by LSD)

4.2.2 Antidepressant Effect of ORG in TST in DD Model Mice

ORG significantly decreased the immobility time in the TST, and the effects were significantly dependent on dose (Table 12). The dose of the best efficacy was 20 mg/kg, and the $ED_{50}$ was about 1.75 mg/kg.

TABLE 12

Dose-immobility time relationship of ORG in TST in DD model mice

| Group | Dose (mg/kg) | Number of animals | Immobility time (s) (mean ± SEM) | P value |
|---|---|---|---|---|
| N.S. | 0.1 ml/10 g | 16 | 185.25 ± 6.66 | |
| ORG | 1.25 | 10 | 171.20 ± 13.02 | 0.392 |
| | 5 | 10 | 146.30 ± 11.66* | 0.018 |
| | 10 | 16 | 145.31 ± 12.41* | 0.006 |
| | 20 | 16 | 140.69 ± 14.138* | 0.002 |
| Imipramine | 15 | 9 | 131.22 ± 10.61* | 0.002 |

*P < 0.05 (one way ANOVA followed by LSD)

EXPERIMENT 5

Antidepressant Effect of ORG in Sleep Deprivation (SD) Model in Mice

Sleep disorder is one of the symptoms of depression. It may be one of the pathological factors that leads to or exacerbates depression. Depression-like behavior such as immobility is enhanced by sleep deprivation. Then, the SD model was used to cause or exacerbate depression and the antidepressant effect of ORG was then tested in FST and TST in SD model mice.

5.1 Experimental Method

Kunming mice (Certificate Number: A4CXK(Chuan) 2003-16) from the Institute of Experimental Animals, People's Hospital of Sichuan Province, were used. They were 3-4 weeks old at the beginning of the experiments and weighed 25-30 g. The numbers of animals in each group are shown in Table 13. ORG was prepared as described in Example 1. Animals were divided into experiment groups with different doses, a vehicle control group, and an imipramine group (Sigma, Batch No. 1061c1588) as positive control.

SD model: A modified method with multiple platforms in a water environment was used to establish the SD model in mice. Mice on the platforms were free to eat and drink. However, if it fell asleep, it fell into the water because of the loss of muscle tone. The fallen animal climbed onto the platform again via a tilt pole which propped up the platforms. After 72 h of sleep deprivation, ORG was administered orally 24 h and 5 h before the FST started. The immobility time of animals were recorded. Methods and data analysis were as described above.

5.2. Results 5.2.1 Antidepressant Effect of ORG on FST in SD Model Mice

On the third day of the three days of sleep deprivation, ORG was administered twice at 24 h and 5 h before the FST started. ORG significantly decreased immobility time in the FST, and the effects were significantly dependent on dose (Table 13). The dose of the best efficacy was 10 mg/kg, and the $ED_{50}$ was about 3.79 mg/kg.

TABLE 13

Dose-immobility time relationship of ORG and TST in SD model mice

| Group | Dose (mg/kg) | Number of animals | Immobility time (s) (mean ± SEM) | P value |
|---|---|---|---|---|
| NS | 0.1 ml/10 g | 26 | 189.27 ± 9.67 | |
| ORG | 1.25 | 10 | 198.00 ± 11.43 | 0.570 |
| ORG | 2.5 | 12 | 177.67 ± 15.95 | 0.421 |
| ORG | 5 | 10 | 160.80 ± 11.64 | 0.064 |
| ORG | 7.5 | 10 | 153.00 ± 11.83* | 0.019 |
| ORG | 10 | 22 | 148.23 ± 7.80* | 0.001 |
| ORG | 20 | 21 | 162.67 ± 9.27* | 0.029 |
| Imipramine | 7.5 | 11 | 150.27 ± 13.17* | 0.009 |

*P < 0.05 (one way ANOVA followed by LSD)

5.3. Therapeutic Index of ORG in DD Model and SD Model Mice

The median toxic dose ($TD_{50}$) of ORG was higher than 1750 mg/kg (see above). The therapeutic index of ORG in DD mice in FST=$TD_{50} \div ED_{50}$=>1750 mg/kg÷1.48 mg/kg=>1182. The therapeutic index of ORG in DD mice in TST=$TD_{50} \div ED_{50}$=>1750 mg/kg÷1.75 mg/kg=>1000. The therapeutic index of ORG in SD mice in FST=$TD_{50} \div ED_{50}$=>1750 mg/kg÷3.79 mg/kg=>462.

EXPERIMENT 6

Pharmacological Study of Anti-Anxiety Effect of ORG

Freezing behavior induced by footshock and conditioned fear stress in rodents are widely accepted as models for evaluating the level of anxiety. Rodents exhibit freezing behavior when aversive stimulation is given. Freezing, which is a normal response of animals to unavoidable fear stimuli, is defined as the complete absence of body movements or maintaining a crouching posture. Anxiolytics reduce the freezing behavior of animals. In addition, the elevated plus maze is a widely accepted model for the evaluation of anxiety in rodents. The assessment of anxiety is based on the conflict between the tendency to novelty exploration and fear of heights, such that the rodent spontaneously spends more time in the closed arm of the elevated plus maze if afraid. Therefore, the novelty exploration behavior is enhanced by anxiolytics and inhibited by anxiogenics.

6.1 Experimental Methods

Kunming mice (Certificate Number: A4CXK(Chuan) 2003-16) from the Institute of Experimental Animals, People's Hospital of Sichuan Province, were used. They were 3-4 weeks old at the beginning of the experiment and weighed 25-30 g. The numbers of animals in each group are shown in Table 13. ORG was prepared as described in Example 1. Animals were divided into drug administration groups with different doses of ORG, a vehicle control group, and a diazepam group (Jinyao Ltd. Co., Batch No. 106k1588) as positive control.

Footshock-induced freezing behavior: Animals received an i.p. injection of ORG or vehicle 24 h and 5 h before being placed in a standard conditioning chamber (Med Associates, USA) for a 10 min training session. Two, 4, 6, 8, and 10 min after the onset of the session, a footshock (0.8 mA, 2 s) was delivered through the grid floor of the chamber. The freezing time during the last 5 min were recorded. Rats were placed in the chamber again without footshock 24 h after the first training, and the freezing time was recorded.

Elevated plus maze (EPM): The EPM had two open and two closed arms of equal size (30 cm long×5 cm wide). The two closed arms were connected by a central 5 cm×5 cm area. The whole maze was elevated to a height of 35 cm. ORG was administered i.p. 24 h and 5 h before the test started. Mice were individually placed in the center of the maze facing a closed arm. Each animal was tested for 5 min in a single session. The number of entrances into open arms, the number of entrances into closed arms, the total time spent in open arms, and the total time spent in closed arms were recorded; a standard of entry was defined as all limbs entering the arm. The number of entrances into open arms and time spent in open arms were the major indexes to evaluate the anxiety level of the animals, for the more entrances or time, the less the anxiety level.

Data analysis: The results of the test are expressed as mean±SEM. One-way ANOVA was used followed by the LSD test with SPSS 11 software. The significance level was set at P<0.05.

6.2 Results 6.2.1 Anti-Anxiety Effect of ORG in the Footshock-Induced Freezing Behavior Test in Rats The freezing time was reduced significantly in rats when ORG was administered intraperitoneally 24 h and 5 h before the test started (Table 14).

TABLE 14

Dose-response relationship of ORG in footshock-induced freezing behavior test in rats

| Group | Dose (mg/kg) | Number of rats | Duration of freezing (s) (mean ± S.E.) | P value |
|---|---|---|---|---|
| NS | 0.1 ml/100 g | 10 | 227.90 ± 20.70 | |
| ORG | 5 | 10 | 203.90 ± 34.09 | 0.523 |
| | 20 | 10 | 100.70 ± 21.78* | 0.002 |

*P < 0.05 (one way ANOVA followed by LSD)

6.2.2 Anti-Anxiety Effect of ORG in the Conditioned Fear Stress-Induced Freezing Behavior Test in Rats The rats were given ORG i.p. twice at 24 h and 5 h before receiving footshocks and re-exposure to the same environment without footshock 24 h later. The fear memory retrieval induced by environmental cues leads to conditioned fear stress-induced freezing behavior in rats. ORG remarkably decreased the freezing behavior (Table 15).

TABLE 15

Dose-response relationship of ORG in the conditioned fear stress-induced freezing behavior test in rats

| Group | Dose (mg/kg) | Number of rats | Duration of freezing (s) (mean ± SEM) | P value |
|---|---|---|---|---|
| NS | 0.1 ml/100 g | 10 | 285.40 ± 47.91 | |
| ORG | 5 | 10 | 310.30 ± 66.19 | 0.776 |
| | 20 | 10 | 95.00 ± 17.73* | 0.004 |

*P < 0.05 (one way ANOVA followed by LSD)

6.2.3 Anti-Anxiety Effect of ORG in the Elevated Plus Maze Test in Mice

ORG administered twice at 24 h and 5 h before the elevated plus maze test significantly increased the number of entrances into open arms and the total time spent in the open arms (Tables 16 and 17). This result indicated a significant anti-anxiety effect of ORG.

TABLE 16

ORG (i.p.) increased the total time spent in the open arms in mice

| Group | Dose (mg/kg) | Number of mice | Total time spent in the open arms (s) (mean ± SEM) | P value |
|---|---|---|---|---|
| NS | 0.1 ml/10 g | 10 | 32.50 ± 8.93 | |
| ORG | 5 | 10 | 50.00 ± 8.99 | 0.151 |
| | 20 | 10 | 16.50 ± 3.60 | 0.188 |
| | 100 | 10 | 70.60 ± 11.56* | 0.003 |
| Diazepam | 2 | 10 | 46.90 ± 7.19 | 0.236 |

*P < 0.05 (one-way ANOVA followed by LSD)

TABLE 17

ORG (i.p.) increased entrances into the open arms in mice

| Group | Dose (mg/kg) | Number of mice | Number of entries into open arms (mean ± SEM) | P value |
|---|---|---|---|---|
| NS | 0.1 ml/10 g | 10 | 3.50 ± 0.87 | |
| ORG | 5 | 10 | 4.50 ± 0.58 | 0.279 |
| | 20 | 10 | 1.80 ± 0.79 | 0.069 |
| | 100 | 10 | 5.90 ± 0.57* | 0.012 |
| Diazepam | 2 | 10 | 4.80 ± 0.77 | 0.161 |

*P < 0.05 (one-way ANOVA followed by LSD)

EXPERIMENT 7

Pharmacological Study of Anti-Stress Effect of ORG

Stress is defined in biological systems as any condition that seriously perturbs the physiological or psychological homeostasis of an organism. Stress is believed to be one of the main factors exacerbating or leading to many illnesses. The hippocampus is a brain formation important in learning and memory as well as in the regulation of stress responses. Stress may lead to the impairment of hippocampal synaptic plasticity, learning, and memory. The concentration of serum corticosterone is one of the most common indications to evaluate stress levels.

7.1 Experimental Methods

Rats weighing 250-300 g, from the Institute of Experimental Animals, People's Hospital of Sichuan Province, were used. ORG was prepared as described in Example 1. Fluoxetine was from Wuhan Yuancheng Technology Co. (Wuhan, China; Batch No: 1004-0801002).

Measurement of serum corticosterone: Radioimmunoassay (RIA; DSL 80100; Texas) was used to determine the effect of ORG on the concentration of serum corticosterone. In the non-stressed group, blood was collected by cardiac puncture under ether anesthesia at 1 h after ORG injection. In the stressed group, 1 h after ORG injection, rats were subjected to elevated platform stress for 30 min, and then were sampled in the same way. The blood samples were kept for 4 h at room temperature and then centrifuged for 15 min (3000 rpm). The supernatant (serum) was collected and stored at −20° C.

Method of long-term potentiation (LTP) recording in hippocampus: Excitatory postsynaptic potentials (EPSPs) in the hippocampus were recorded to determine the anti-stress effect of ORG. Stress impairs LTP in the CA1 area of hippocampus, and this can be rescued by anti-stress drugs. Rats were stressed by footshock as follows: 1 mA, 2 s, 5 times at intervals of 2 min. Hippocampal slices were prepared, incubated for 1 h at 34-36° C., and then kept at room temperature. ORG was applied in the bath solution. EPSPs mediated by NMDA and AMPA receptors in the CA1 region were recorded until the baseline was stable for 20 min. Then high frequency stimulation (HFS, 100 Hz, 100 pulses, 20 s interval) was used to induce LTP. The EPSPs were recorded for 1 h after HFS.

Data Analysis: Data are expressed as mean±SEM and LTP is expressed as the percentage of the average amplitude of the last 10 min relative to the baseline. One-way ANOVA was used followed by the LSD test with SPSS 11 software. The significance level was set at $P<0.05$.

7.2 Results 7.2.1 Anti-Stress Effect of ORG (i.p.) on Acute Stress-Induced Elevation of Serum Corticosterone Level.

Blood was collected by cardiac puncture 1 h after i.p. injection of ORG in controls or after 30 min stress experience. ORG significantly decreased the level of serum corticosterone in a dose-dependent manner (Table 18).

TABLE 18

Dose-corticosterone level relationship of ORG (i.p.)

| Groups | Dose (mg/kg) | Number of animals | Concentration of serum corticosterone (ng/ml) (mean ± SEM) | P value |
|---|---|---|---|---|
| Non-stress + NS | 0.1 ml/100 g | 16 | 116.06 ± 27.84 | |
| Non-stress + ORG | 0.875 | 8 | 209.02 ± 52.77 | 0.197 |
| | 3.5 | 8 | 166.06 ± 41.90 | 0.649 |
| | 14 | 16 | 70.04 ± 14.75 | 0.084 |
| | 28 | 8 | 63.13 ± 22.21 | 0.122 |
| Non-stress + Fluoxetine | 15 | 16 | 167.20 ± 31.35 | 0.559 |
| | 30 | 8 | 178.14 ± 38.77 | 0.490 |
| Stress + NS | 0.1 ml/100 g | 16 | 324.30 ± 48.81 | |
| Stress + ORG | 0.875 | 8 | 349.85 ± 61.75 | 0.706 |
| | 3.5 | 8 | 263.63 ± 49.14 | 0.372 |
| | 14 | 16 | 237.63 ± 32.45 | 0.120 |
| | 28 | 8 | 137.41 ± 26.84* | 0.007 |
| Stress + Fluoxetine | 15 | 16 | 331.35 ± 46.43 | 0.899 |
| | 30 | 8 | 324.58 ± 58.63 | 0.997 |

*$P < 0.05$ (one-way ANOVA followed by LSD)

7.2.2 Restoration Effect of ORG on Stress-Impaired Hippocampal LTP

Hippocampal slices were prepared from rats after exposure to footshock stress, which is a well accepted protocol to impair hippocampal LTP. In slices incubated with ORG for 1 h, baseline EPSPs were recorded for 20 min. ORG restored the stress-impaired LTP and even increased LTP significantly at the dose of 5 μM/L, showing a dose-dependent effect (Table 19).

The above results show that ORG has a significant anti-stress effect and has important clinical value in treating depression with a stress etiology.

TABLE 19

Dose-effect relationship in hippocampal slices incubated with ORG on restoration of stress-impaired LTP

| Groups | Dose | Number of slices | Average of last 10 min (mean ± SEM) | P value |
|---|---|---|---|---|
| Control | | 9 | 134.52 ± 10.71 | |
| Control + ORG | 5 μM | 11 | 122.93 ± 3.75 | 0.453 |

TABLE 19-continued

Dose-effect relationship in hippocampal slices incubated with ORG on restoration of stress-impaired LTP

| Groups | Dose | Number of slices | Average of last 10 min (mean ± SEM) | P value |
|---|---|---|---|---|
| FS + NS | 0.1 ml/10 g | 11 | 113.22 ± 6.77 | 0.234 |
| FS + ORG | 50 nM | 9 | 128.99 ± 7.30 | 0.732 |
| FS + ORG | 5 μM | 8 | 189.56 ± 23.6* | 0.002 |

*$P < 0.05$ (one-way ANOVA followed by LSD)

EXPERIMENT 8

Pharmacological Study of ORG and Enhancement of Learning and Memory

The Morris water maze (MWM) is widely used in studies of hippocampus-dependent learning and memory and its cellular and molecular mechanisms. It is well accepted that the MWM is an effective method of pharmacological evaluation of learning and memory. Escape latency, strategy, and trajectory of the animals are automatically tracked and analyzed to investigate their spatial learning and memory. After the animals learn how to escape, the hidden platform is removed to test the retention in the target quadrant. A longer time spent in the right quadrant indicates a better memory.

8.1 Experimental Methods

Kunming mice (Certificate Number: A4CXK(Chuan) 2003-16) from the Institute of Experimental Animals, People's Hospital of Sichuan Province, were used. They were 3-4 weeks old at the beginning of the experiment and weighed 25-30 g. Numbers of animals in each group are shown in Tables 20 and 21. ORG was prepared as described in Example 1. Animals were divided into drug administration groups with fluoxetine or different doses of ORG and a vehicle control group. The drug administration groups received 1.75 mg/kg or 3.5 mg/kg of ORG or 15 mg/kg of fluoxetine. Animals received a single i.p. injection of drug or vehicle 30 min either after training every day or 30 min before the retention test on day 8.

Morris water maze: The MWM was performed in a circular pool (100 cm in diameter and 36 cm in depth) with a hidden platform (10 cm×10 cm) that was approximately 1 cm below the water surface. The pool was surrounded by yellow curtains with different shaped markers hanging in each quadrant. The time spent to find the hidden platform and the trajectory of the mouse were recorded by computer. From days 1 to 7, mice were placed in the pool to find the fixed hidden platform. On day 8, the platform was removed and the time that the mouse spent in the target quadrant was counted in 1 min of free swimming.

Data analysis: The results of the test are expressed as mean±SEM. One-way ANOVA was used followed by the LSD test with SPSS 11 software. The significance level was set at $P<0.05$.

8.2. Results 8.2.1 Effect of ORG (i.p.) Immediately After Training in the MWM Test When ORG was given after daily training, the spatial memory retrieval (the time that animals spent in the target quadrant) was enhanced significantly by influencing memory consolidation (Table 20).

TABLE 20

Spatial memory was enhanced in mice with
daily ORG administration after training

| group | Dose (mg/kg) | Number of mice | Time spent in the right quadrant (s) (mean ± SEM) | P value |
|---|---|---|---|---|
| NS | 0.1 ml/10 g | 10 | 27.10 ± 2.79 | |
| ORG | 1.75 | 10 | 28.18 ± 1.70 | 0.74 |
| ORG | 3.5 | 10 | 34.24 ± 2.01* | 0.03 |
| Fluoxetine | 15 | 9 | 32.61 ± 2.20 | 0.11 |

*P < 0.05 (one-way ANOVA followed by LSD)

8.2.2 Effect of ORG (i.p.) Before Retrieval in the MWM Test

Training was finished after 7 days. The retrieval test was carried out on day 8. When ORG was administered 30 min before retrieval, spatial memory retrieval was enhanced significantly (Table 21).

TABLE 21

Spatial memory was enhanced in mice with
ORG administered 30 min before retrieval

| Group | Dose (mg/kg) | Number of mice | Time spent in the right quadrant (s) (mean ± SEM) | P value |
|---|---|---|---|---|
| NS | 0.1 ml/10 g | 10 | 27.95 ± 2.19 | |
| ORG | 1.75 | 10 | 29.38 ± 2.16 | 0.65 |
| ORG | 3.5 | 10 | 35.52 ± 2.43* | 0.02 |
| Fluoxetine | 15 | 9 | 29.44 ± 2.14 | 0.65 |

*P < 0.05 (one-way ANOVA followed by LSD)

EXPERIMENT 9

Toxicity Test of ORG 9.1 Acute Toxicity Test of ORG in Mice
9.1.1 Experimental Methods Kunming mice (Certificate Number: A4CXK(Chuan) 2003-16) from the Institute of Experimental Animals, People's Hospital of Sichuan Province, were used. They were 3-4 weeks old and at the beginning of the experiment and weighed 25-30 g. ORG was prepared as described in Example 1. ORG (1750 mg) was dissolved in 10 ml NS to give a concentration of 175 mg/ml. Mice were divided into two groups, the ORG group for evaluation was given ORG and a group was treated with NS for vehicle control. ORG and NS were given to each group orally at a volume of 0.1 ml/10 g.
9.1.2. Results When ORG was administered at 1750 mg/kg to mice in an acute toxicity test, the appearance, behavior, mental status, appetite, hair, color, and breathing of the animals were observed for 14 days and nothing abnormal was found. All mice survived the experiment and the weight gain was normal. There was no significant difference between the two groups. All mice were sacrificed on day 14, and the heart, liver, spleen, lung, kidney, pancreas, ovary, testis, small intestine, and other visceral organs were investigated by pathological section and also had no evident abnormalities.
9.2 Subacute Toxicity Test of ORG in Rats
9.2.1 Experimental Methods Rats (Certificate Number: A4CXK(Chuan)2003-16) from the Institute of Experimental Animals, People's Hospital of Sichuan Province, were used. Their weight was 250-300 g. ORG was prepared as described in Example 1.
9.2.2 Results ORG (1750 mg/kg), which is 7955 times the $ED_{50}$ in mouse FST and 2397 times the $ED_{50}$ in mouse TST, was administered orally once per day for 14 consecutive days. The appearance, behavior, mental status, appetite, hair, color, and breathing of the animals were observed for 14 days and nothing abnormal was found. All rats survived the experiment and the weight gain was normal. There was no significant difference between the two groups. All rats were sacrificed on day 14, and the heart, liver, spleen, lung, kidney, pancreas, ovary, testis, small intestine, and other visceral organs were investigated by pathological section and images of the tissue sections showed no evident abnormalities.

Pharmacological Summary of
5-methyl-1,3-benzenediol and its Derivatives

The dose-effect and time course-response of antidepressant effects of ORG and its derivatives were studied using the models FST, TST, DD, SD, and CMS. The results indicate that OR, ORG and its derivatives exhibit activities useful to treat and prevent depression and the symptoms suggesting depression: circadian rhythm disorders, sleep disorders, and chronic stress. Studies of the antidepressant mechanism showed that OR, ORG and its derivatives repair the impairment of hippocampal LTP, enhance hippocampus-dependent learning and memory, and treat and prevent depression-related factors such as anxiety and acute stress. The mechanism of hippocampal LTP is mainly related to NMDA and AMPA receptors and their molecular and cellular pathways. In conclusion, OR, ORG and its derivatives may adjust these targets as regulators and produce the effects of treating and preventing depression through restoring hippocampal LTP.

Since neurons mainly communicate via chemical synapses, and memories are believed to be stored within these synapses, LTP is considered to be one of the major cellular mechanisms underlying learning and memory. Therefore, OR, ORG and its derivatives can also be applied to treat and prevent other disorders such as Alzheimer's disease, childhood ADHD, autism, and schizophrenia. Since more than 90% of all diseases can be induced or exacerbated by stress and the hippocampal functions of stress regulation involve synaptic plasticity, OR, ORG and its derivatives may be beneficial in the treatment, prevention, and rehabilitation of many diseases in the clinic, for example, drug addicts who experience extreme stress during the withdrawal period, and cancer or cardiovascular disease patients who undergo excessive stress or anxiety.

Combined with the results of the preliminary experiments on toxicity, OR, ORG and its derivatives have new applications in the treatment and prevention of depression and etiological causes of depression with characteristics of high efficiency and low toxicity. Other uses of OR, ORG and its derivatives are applications in the treatment and prevention of symptoms suggesting depression such as acute stress and anxiety. The mechanisms involved in the antidepressant effect of OR, ORG and its derivatives are the regulation of serum corticosteroids, hippocampal synaptic plasticity including NMDA and AMPA receptors and their intracellular signaling pathways, and learning and memory.

Therefore, the therapeutic uses and beneficial effects of the present invention of OR, ORG and its derivatives are as follows: (1) therapeutic effect on depression; (2) therapeutic effects on the causes of depression; (3) therapeutic effects on the symptoms of depression or similar symptoms of other diseases; (4) their potential uses are not intended and should not be construed to be limited in any way to treating and preventing depression, and may also be useful for other diseases involving stress, anxiety, and cognitive functional impairment.

The invention claimed is:

1. A method of treating a disorder, said method comprising administering to a patient having the disorder a composition comprising a substance represented by Formula I:

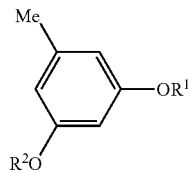

wherein:
- the disorder is a member selected from the group consisting of depression, circadian rhythm disorders, sleep disorders, chronic stress disorders, anxiety disorders, acute stress-induced impairment disorders, and cognitive functional impairment disorders;
- the composition is effective to treat the disorder;
- $R^1$ is hydrogen, β-D-glucopyranosyl, β-D-glucopyranosyl-(1→6)-β-D-glucopyranosyl, 2,3,4,6-tetra-O-acetyl-β-D-glucopyranosyl, mannosyl, allosyl, galactosyl, rhamnopyranosyl, fucosyl, xylosyl, arabinosyl, acetyl, propionyl, benzoyl, cinnamoyl, succinyl, methyl, ethyl, propyl, butyl or benzyl; and
- $R^2$ is hydrogen.

2. The method according to claim 1, wherein $R^1$ is hydrogen, β-D-glucopyranosyl, β-D-glucopyranosyl-(1→6)-β-D-glucopyranosyl, 2,3,4,6-tetra-O-acetyl-β-D-glucopyranosyl, mannosyl, allosyl, galactosyl, rhamnopyranosyl, fucosyl, xylosyl, or arabinosyl.

3. The method according to claim 2, wherein $R^1$ is hydrogen, β-D-glucopyranosyl, β-D-glucopyranosyl-(1→6)-β-D-glucopyranosyl.

4. The method according to claim 1, wherein the disorder is at least one member selected from the group consisting of depression, manic depression, mixed depression, manic disorder, hypomania, depressive disorder, dysthymia, affective disorders, bipolar disorder and bipolar affective disorder containing two or more episodes of depression and hypomania, and alternating episodes of mania and depression.

5. The method according to claim 1, wherein the composition is 5-methyl-1,3-benzenediol or a derivative thereof.

6. The method according to claim 1, wherein the composition is a functional food.

7. The method according to claim 1, wherein the composition is an antidepressant comprising in addition to the substance represented by Formula I pharmaceutically acceptable carriers or excipients.

8. The method according to claim 7 wherein, $R^1$ is hydrogen, β-D-glucopyranosyl, β-D-glucopyranosyl-(1→6)-β-D-glucopyranosyl, 2,3,4,6-tetra-O-acetyl-β-D-glucopyranosyl, mannosyl, allosyl, galactosyl, rhamnopyranosyl, fucosyl, xylosyl, or arabinosyl.

9. The method according to claim 8, wherein $R^1$ is hydrogen, β-D-glucopyranosyl or β-D-glucopyranosyl-(1→6)-β-D-glucopyranosyl.

10. The method according to claim 7, wherein an effective dosage of the substance to treat depression is from 0.1 mg/adult/day to 12 g/adult/day.

11. The method according to claim 10, wherein the effective dosage of the substance is 50-200 mg/adult/day.

* * * * *